US011154292B2

(12) United States Patent
Meister et al.

(10) Patent No.: US 11,154,292 B2
(45) Date of Patent: Oct. 26, 2021

(54) IMPLANTABLE TEXTILE ANCHOR

(71) Applicant: MEISTER & CIE AG HASLE-RÜEGSAU, Hasle-Rüegsau (CH)

(72) Inventors: Marcel Meister, Hasle-Rüegsau (CH); Philippe Gédet, Ipsach (CH)

(73) Assignee: MEISTER & CIE AG HASLE-RÜEGSAU, Hasle-Rüegsau (CH)

( * ) Notice: Subject to any disclaimer, the term of this patent is extended or adjusted under 35 U.S.C. 154(b) by 239 days.

(21) Appl. No.: 16/075,875

(22) PCT Filed: Jan. 20, 2017

(86) PCT No.: PCT/EP2017/051147
§ 371 (c)(1),
(2) Date: Aug. 6, 2018

(87) PCT Pub. No.: WO2017/133903
PCT Pub. Date: Aug. 10, 2017

(65) Prior Publication Data
US 2019/0038277 A1 Feb. 7, 2019

(30) Foreign Application Priority Data
Feb. 5, 2016 (EP) .................................... 16154504

(51) Int. Cl.
*A61B 17/04* (2006.01)
(52) U.S. Cl.
CPC .. *A61B 17/0401* (2013.01); *A61B 2017/0403* (2013.01); *A61B 2017/0409* (2013.01); *A61B 2017/0459* (2013.01)

(58) Field of Classification Search
CPC ........ A61B 17/0401; A61B 2017/0409; A61B 2017/0459; A61F 2/0811; A61F 2002/0852; D04C 3/40
See application file for complete search history.

(56) References Cited

U.S. PATENT DOCUMENTS 7,601,165 B2  10/2009  Stone
7,608,098 B1  10/2009  Stone
(Continued)

FOREIGN PATENT DOCUMENTS

RU        2116802 C1    8/1998

OTHER PUBLICATIONS

International Search Report, dated Aug. 22, 2017, from corresponding PCT/EP2017/051147 application.
(Continued)

*Primary Examiner* — Katherine M Rodjom
(74) *Attorney, Agent, or Firm* — Nixon & Vanderhye

(57) ABSTRACT

The implantable textile anchor includes a collapsible member including a first end, a second end and a plurality of eyelets arranged between the first end and the second end, and at least one filament. The collapsible member is braided to form bifurcating and converging portions, which define the eyelets. The at least one filament is guided through eyelets of the collapsible member so that by pulling on the at least one filament the collapsible member collapses to a form with an increased lateral extension. The at least one filament is knotted to an eyelet and/or the at least one filament and at least a second filament are made integral with the collapsible member.

20 Claims, 8 Drawing Sheets

(56) References Cited

U.S. PATENT DOCUMENTS

| | | | |
|---|---|---|---|
| 7,658,751 B2 | 2/2010 | Stone et al. | |
| 7,749,250 B2 | 7/2010 | Stone et al. | |
| 7,857,830 B2 | 12/2010 | Stone et al. | |
| 7,905,903 B2 | 3/2011 | Stone et al. | |
| 8,361,113 B2 | 1/2013 | Stone et al. | |
| 9,173,645 B2 | 11/2015 | Overes et al. | |
| 9,445,803 B2 | 9/2016 | Marchand et al. | |
| 9,610,077 B2 | 4/2017 | Allen | |
| 9,962,149 B2 | 5/2018 | Brown et al. | |
| 2009/0062850 A1* | 3/2009 | Ken | A61B 17/0057 606/215 |
| 2009/0318961 A1 | 12/2009 | Stone et al. | |
| 2011/0264141 A1* | 10/2011 | Denham | A61B 17/06166 606/232 |
| 2011/0270278 A1* | 11/2011 | Overes | A61B 17/842 606/144 |
| 2012/0197271 A1* | 8/2012 | Astorino | A61B 17/0057 606/148 |
| 2013/0018416 A1* | 1/2013 | Lombardo | A61B 17/06166 606/232 |
| 2013/0123810 A1 | 5/2013 | Brown et al. | |
| 2013/0131722 A1 | 5/2013 | Marchand et al. | |
| 2014/0243893 A1 | 8/2014 | Santangelo et al. | |
| 2015/0045831 A1 | 2/2015 | Allen | |
| 2016/0354079 A1 | 12/2016 | Marchand et al. | |
| 2017/0296182 A1 | 10/2017 | Allen | |

OTHER PUBLICATIONS

Office Action issued in Chinese Patent Application No. 201780015482 dated Jul. 15, 2020, with partial English translation provided.
Office Action issued in Russian Patent Application No. 2018131572/14(051515) dated Apr. 13, 2020, with English translation provided.
Search Report issued in Russian Patent Application No. 2018131572/14(051515) dated Apr. 13, 2020, with English translation provided.

* cited by examiner

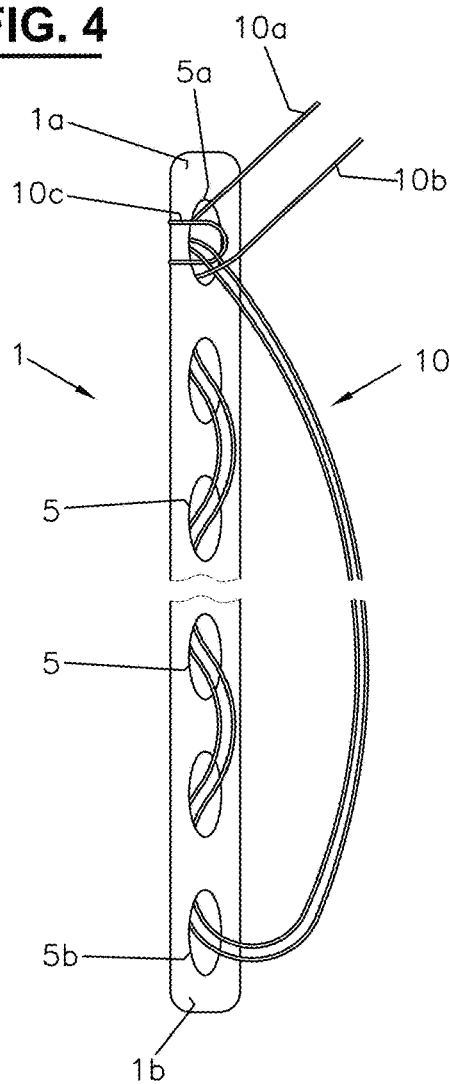
FIG. 4
FIG. 5
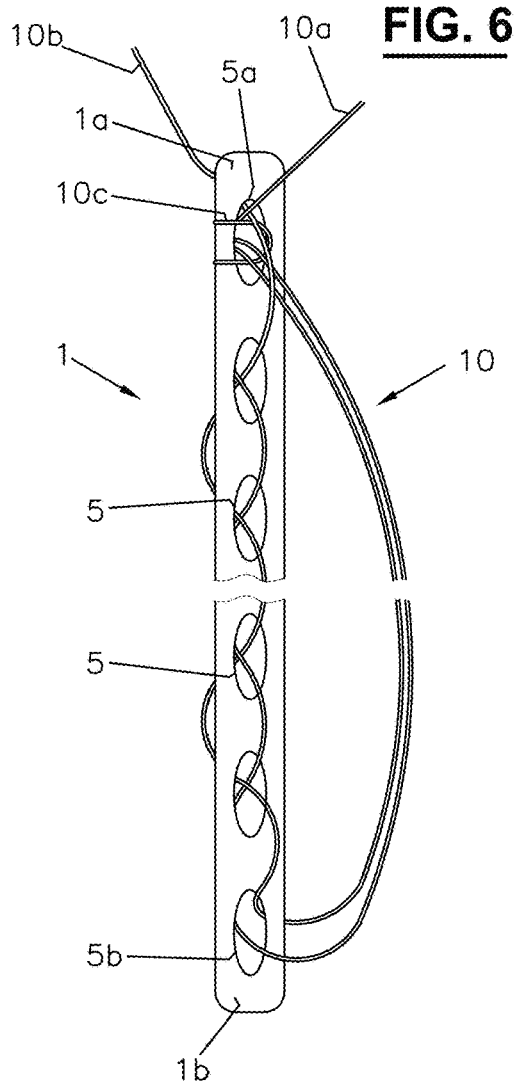
FIG. 6
FIG. 7
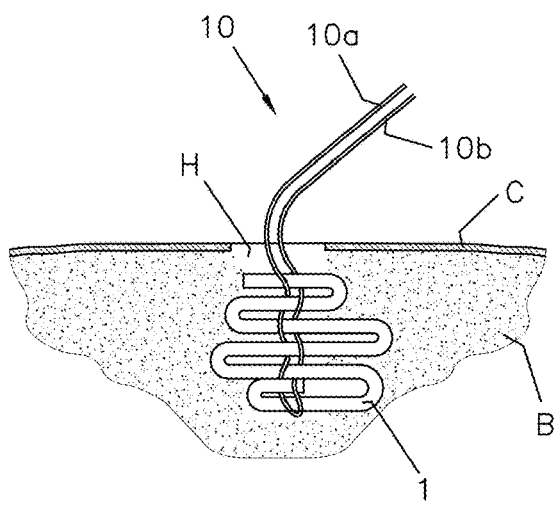
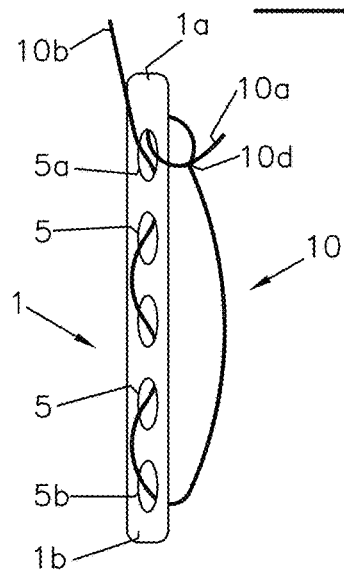

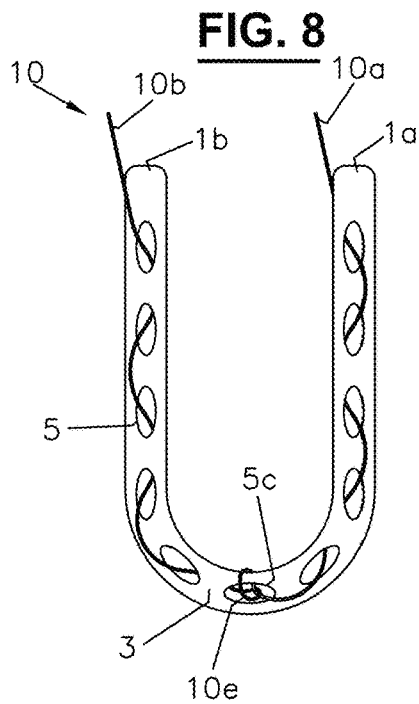
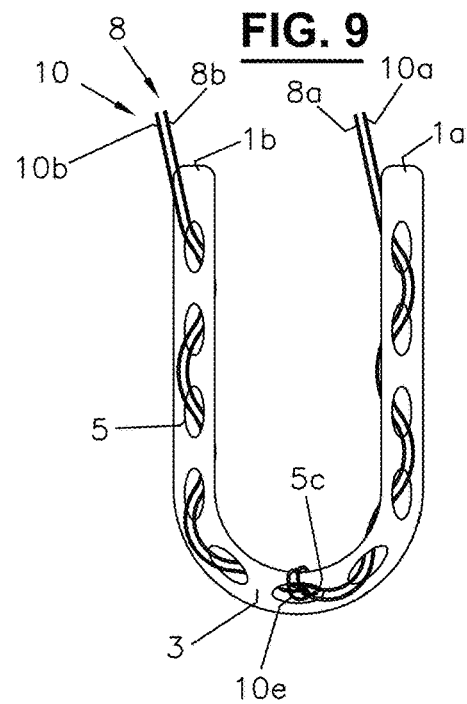
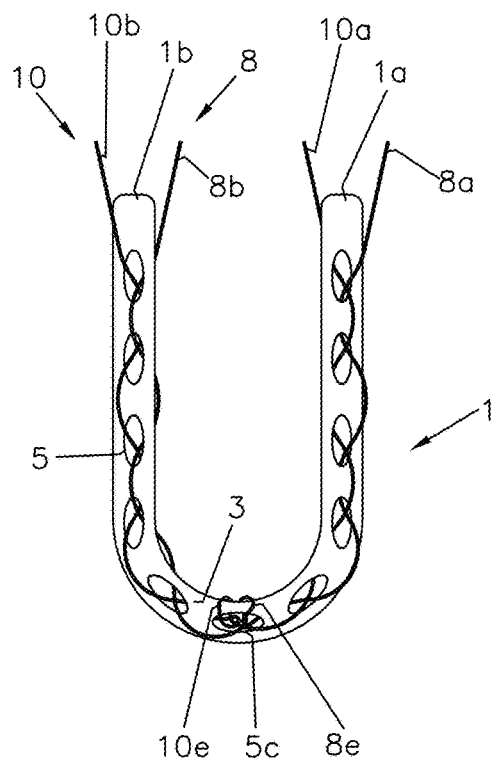
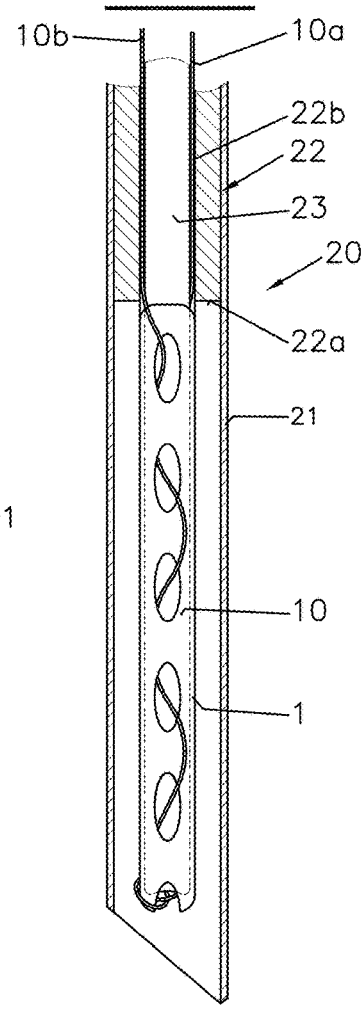
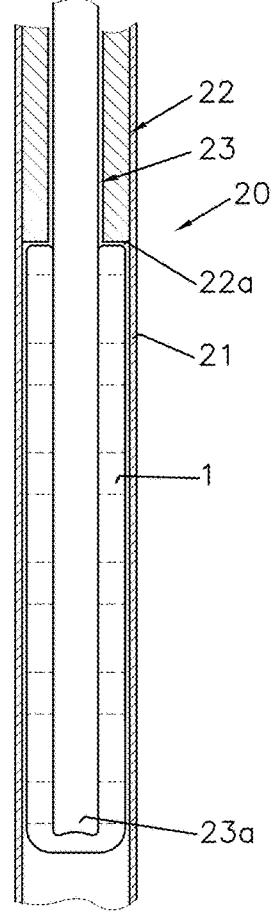

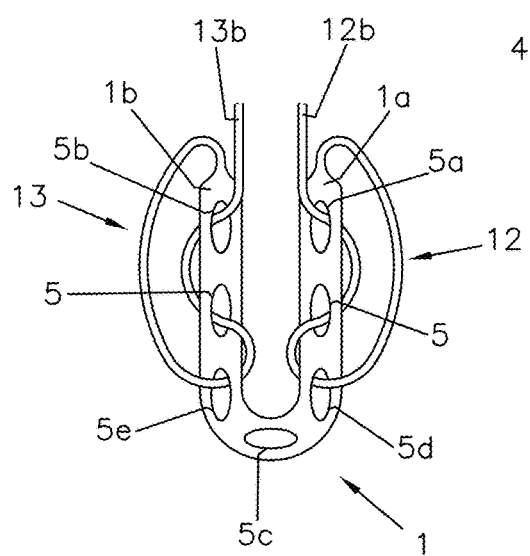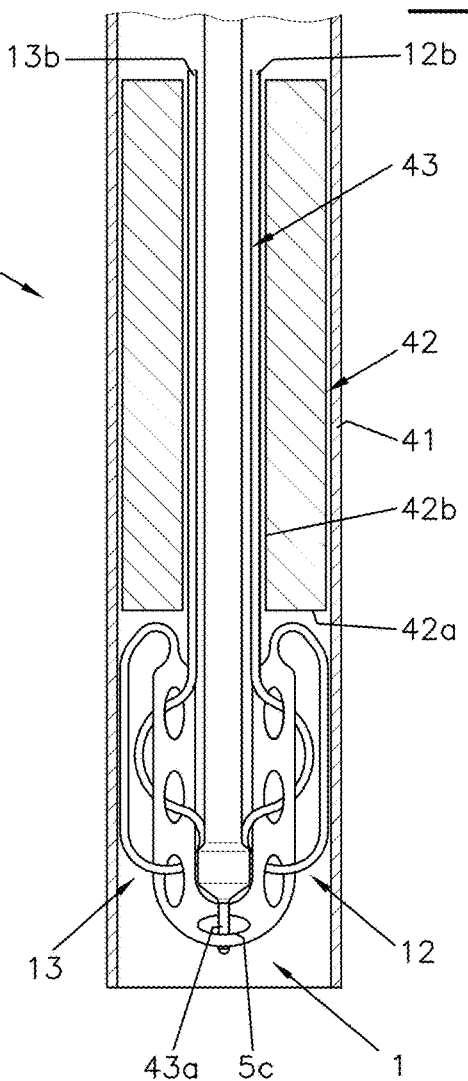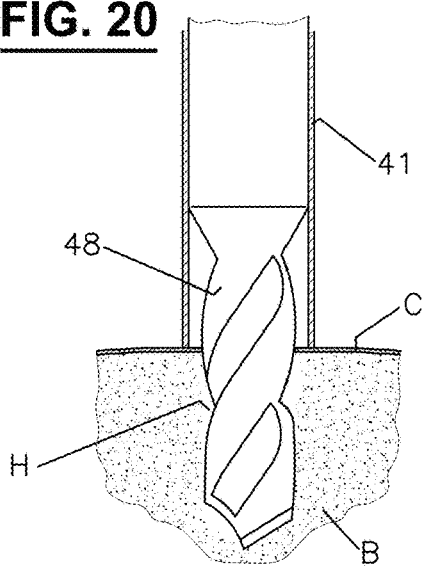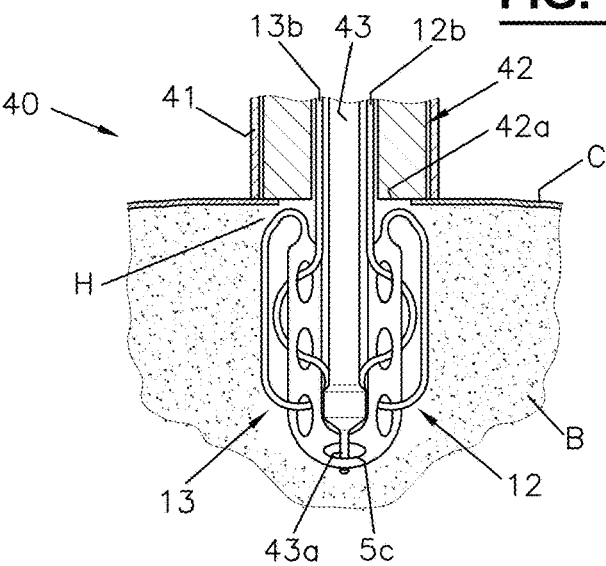

IMPLANTABLE TEXTILE ANCHOR

BACKGROUND OF THE INVENTION

Field of the Invention

The invention relates to an implantable textile anchor comprising a collapsible member and at least one filament for collapsing the member.

Surgical procedures often involve the use of fixation means, which are fastened e.g. in a hole produced in a bone or soft tissue. Textile anchors, for instance in the form of so-called "all-suture based anchors", can be used as such fixation means. In use, the textile anchor is inserted into the hole in an initial state, in which it has a slender form, and then transformed into a collapsed state, in which the anchor has a laterally expanded form, whereby it is fixed in the hole. One specific example is arthroscopic surgery on the shoulder or knee, in which an anchor is installed into bone, and a filament serving as a suture is threaded through the tissue (such as a ligament, tendon, or cartilage) which is to be attached to the bone. The suture is then secured to fasten the tissue in place.

Description of the Related Art

The documents U.S. 2013/123810 A1 and U.S. 2013/131722 A1 disclose textile anchors suitable as fixations means. However, their fabrication is relatively complicated.

The document U.S. 2011/0270278 A1 discloses an anchor including an anchor body, which is formed by a braided strand having a plurality of openings and with which an actuation strand can be made integral. Only one end is available for handling, which makes it difficult to securely fix the anchor. The document discloses another anchor including an anchor body, which is formed by a mesh and which has an eyelet. The actuating strand is put therethrough without any attachment. This has the risk that the strand may be displaced so that the anchor cannot be securely fixed.

The document U.S. 2009/0318961 A1 discloses a suture construction with a braided body, in which a hollow passage is formed. This construction is not configured to be used as a textile anchor.

BRIEF SUMMARY OF THE INVENTION

It is an aim of the present invention to provide for a textile anchor which simplifies its fabrication and which is adapted to be securely fixed.

This aim is achieved by the anchor as defined in claim 1. The further claims specify preferred embodiments of the anchor, a set with at least one anchor and an instrument, and a method for producing an anchor.

The provision of an anchor comprising a collapsible member which is braided to form bifurcating and converging portions which define eyelets allows a simplified fabrication, as it is e.g. not necessary to create manually a plurality of loops for defining openings. The eyelets of the collapsible member define definite openings in the member for guiding through a filament.

In use, the anchor can be securely fixed by the provision of at least one filament, which is knotted to an eyelet and/or which together with at least a second filament is made integral with the collapsible member.

Preferably, the anchor comprises one or more of the following features:

- The at least one filament is formed separately from the collapsible member.
- The at least one filament is knotted to an eyelet to form an attachment location on the collapsible member. Thereby, the at least one filament is attached to the collapsible member, so that the attachment location is not shifted relative to the eyelet when pulling on one end of the at least one filament.
- The at least one filament is knotted to an eyelet by forming at least one loop from a first portion of the at least one filament and by guiding another portion of the at least one filament, e.g. one or both of its end, through the loop.
- The bifurcating and converging portions of the collapsible member comprise branch portions, which border the eyelets, wherein the at least one filament is knotted to an eyelet by guiding a portion of the at least one filament around at least one of said branch portions to form a loop, through which a portion of the at least one filament is guided through.
- The at least one filament includes a first end and the at least one or the least second filament includes a second end, wherein the collapsible member includes at least one eyelet, through which the first and second ends are guided from different sides of the collapsible member.
- The at least one filament is separate from the collapsible member and guided through eyelets such that the first end of the at least one filament extends from the first end of the collapsible member and the second end of the at least one filament extends from the second end of the collapsible member, such that the first and second ends of the at least one filament are accessible for pulling thereon.
- The at least one filament and the at least second filament, which are made integral with the collapsible member, are guided through eyelets of the collapsible member so that by pulling on the filaments the collapsible member collapses to a form with an increased lateral extension.
- The at least one filament and the at least second filament are guided through eyelets such that the first end of the at least one filament extends from the first end of the collapsible member and the second end of the at least second filament extends from the second end of the collapsible member, such that the first end of the at least one filament and the second end of the at least second filament are accessible for pulling thereon.
- The anchor comprises at least two filaments, which have a different color and/or a different pattern. For instance, the pattern may be different in that the fraction of threads having a particular color is different for each filament.
- The collapsible member is configured as an elongated structure, which extends from the first end to the second end.
- The eyelets in the collapsible member define openings extending transversally through the collapsible member so that the at least one filament is guided through the eyelets transversally to the collapsible member.
- The collapsible member has more than two eyelets, in particular more than three eyelets.

BRIEF DESCRIPTION OF THE DRAWINGS

Additional features and their advantages will be become apparent from the following description of exemplary embodiments and from the drawings, where

FIG. 4 shows an embodiment of an anchor of a first kind;

FIG. 5 shows the anchor of FIG. 4 applied in a bone;

FIG. 6 shows another embodiment of an anchor of a first kind;

FIG. 7 shows a further embodiment of an anchor of a first kind;

FIG. 8 shows a further embodiment of an anchor of a first kind;

FIG. 9 shows a further embodiment of an anchor of a first kind;

FIG. 10 shows a further embodiment of an anchor of a first kind;

FIG. 11 shows a set with an instrument and an anchor of a first kind according to FIG. 8 in a partly sectioned side view, wherein the instrument and the anchor are shown only in part;

FIG. 12 shows the set of FIG. 11 in a partly sectioned front view;

FIG. 18 shows an embodiment of an anchor of a second kind;

FIG. 19 shows a set with an instrument and an anchor of a second kind in a partly sectioned front view, wherein the instrument and the anchor are shown only in part;

FIG. 20 shows schematically part of a drill for drilling a hole in a bone;

FIG. 21 shows the set of FIG. 19 applied for the hole of FIG. 20;

DETAILED DESCRIPTION OF THE PREFERRED EMBODIMENTS

Embodiments of an Anchor a First Kind

Figure 1:
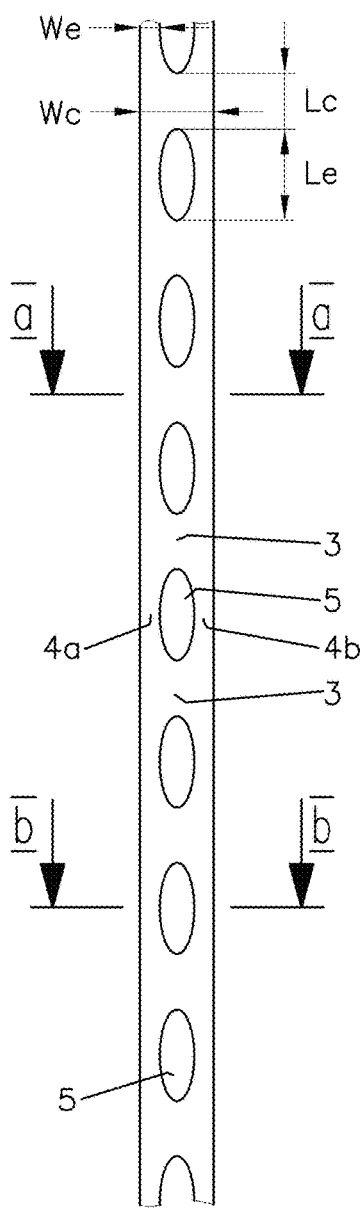
FIG. 1 shows a braided structure for producing an anchor of a first kind.

FIG. 1 shows a flexible slender structure, which comprises a plurality of eyelets 5 passing therethrough. Thus, an eyelet 5 defines an opening which extends from one side of the structure to its other side. To form a collapsible member 1 for an anchor of a first kind shown in FIG. 4-10, 13-15, a portion with a predetermined length is cut off from the structure of FIG. 1. The latter is a textile which is braided such that, in an alternating fashion, it bifurcates at a central portion 3 into two separated branch portions 4a, 4b, which converge again at an adjacent central portion 3 to form an eyelet 5. The length Lc of the central portions 3 and the length Le of the eyelets 5 may be the same or may vary. In FIG. 1 each central portion 3 is shown as having the same width Wc and each branch portion 4a, 4b is shown as having the same width We. It is also conceivable that the width Wc of the central portions 3 and/or the width We of the branch portions 4a, 4b vary.

Figure 2A:
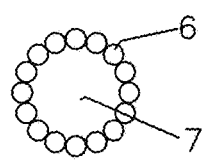
FIGS. 2a and 2b are an enlarged view of an example of a possible tubular cross-section, which the structure of FIG. 1 may have, when sectioned along line a-a and line b-b, respectively.
Figure 2B:
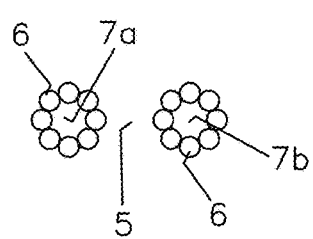
Figure 3A:
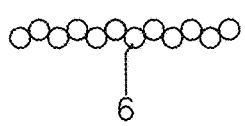
FIGS. 3a and 3b are an enlarged view of a flat cross-section, which the structure of FIG. 1 has in an example not being part of the invention, when sectioned along line a-a and line b-b, respectively.
Figure 3B:
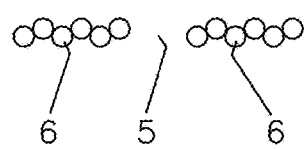

The braiding is done such that the strands 6 form a tubular structure including tubular central portions 3 which bifurcate into two tubular branches 4a, 4b at an eyelet 5. This kind of structure is apparent from FIG. 2a, 2b. Optionally, the interior 7, 7a, 7b of these formed tubes may include a core. The core may include for instance strands, which are straight, twisted or braided. The core may be made of one or more of the following materials: textile material, non-textile material, metal, plastic, etc. The core may include e.g. a tube, in particular a plastic tube, a monofilament, a monofilament with embedded particles that can be released over time (drug delivery system), a metal wire, a mesh, a webbing, etc.

Machines arranged for tubular braiding cause the yarn carriers to move in a circle. This results in a tubular structure having an interior, which may or may not include a core. Machines arranged for flat braiding cause the yarn carriers to move on a line back and forth. This results in a flat structure without an interior.

FIG. 4 shows an example of an anchor comprising a collapsible member 1 having a first end 1a, a second 1b as well as a plurality of eyelets 5 arranged therebetween and a filament 10 passed through at least some of the eyelets 5. The collapsible member 1 may be produced e.g. by cutting off a portion from the structure of FIG. 1. Here, the filament 10 is a flexible member separate from the collapsible member 1 and may have a suture- or lace-like structure.

The filament 10 is interconnected with the collapsible member 1 such that when pulling thereon the member 1 collapses to form a folded structure having an increased lateral extension (see FIG. 5). In the following, the side of the member 1 visible in FIG. 4 is designated as the front side, while the non-visible side is the rear side. Here, the filament 10 is folded in the middle to form a loop portion 10c arranged at the front side of the member 10. Both ends 10a and 10b of the filament 10 are passed from the rear side of the member 1 through the first eyelet 5a arranged at the end 1a and through the loop portion 10c, so that a knot is formed, and are directed through the last eyelet 5b arranged at the end 1b. Subsequently, the two ends 10a, 10b are guided together in alternating fashion through the eyelets 5 from one side of the member 1 to the other side. Finally, the ends 10a, 10b are led once more straight through the first eyelet 5a.

FIG. 5 shows an example of an anchor 1, 10 implanted in the bone B of a patient. (The layer C refers to the cortex, which is the outer shell of the bone B.) In use, the surgeon drills a hole H into the bone B, pushes the member 1 thereinto by means of a suitable instrument and pulls on the ends 10a, 10b of the filament 10, so that the member 1 adopts a collapsed structure, which is firmly anchored in the bone B.

FIG. 6 shows a variant of the anchor of FIG. 4, in which the ends 10a and 10b of the filament 10 are guided from the last eyelet 5b to the first eyelet 5a not in parallel, but in a crossed fashion. Thus, the ends 10a and 10b pass through opposite sides at each eyelet 5, 5a, 5b.

FIG. 7 shows a variant of the anchor, in which the first end 10a of the filament 10 is directed through the first eyelet 5a of the member 1 and knotted together at a position 10d. The other (free) end 10b is directed through the last eyelet 5b and is led subsequently in an alternating manner through the eyelets 5 from one side of the member 1 to the other side. In this variant, the anchor 1, 10 forms a so-called single-filament-loaded anchor, which has only one end 10b utilizable for fixation.

FIG. 8 shows another variant of the anchor, in which the filament 10 is directed through the eyelets 5 alternatingly from one side of the member 1 to its other side. In addition, the filament 10 is fixed in the area of the middle of the member 1, so that it cannot be shifted as a whole relative to the member 1. For this purpose, the filament 10 is guided e.g. through the eyelet 5c to form a knot 10e. It is conceivable to provide for a second filament 8 which is guided through the eyelets 5 in parallel with the filament 10 as shown in FIG. 9. The second filament 8 is attached in the middle of the member 1, for instance it is knotted to a branch portion of the eyelet 5c in a similar way as the filament 10.

FIG. 10 shows a variant of the anchor of FIG. 9, in which the first filament 10 and the second filament 8 are guided through the eyelets not in parallel, but in a crossed manner. Thus, the filaments 8 and 10 pass through opposite sides at each eyelet. The first and second filaments 8, 10 are guided e.g. through the eyelet 5c to form a knot 8e and a knot 10e, respectively.

FIGS. 11 and 12 show part of an instrument 20 suitable to apply an anchor at a specific location in the body of a patient. The instrument 20 comprises a cannula 21 defining a tube which is open at the distal end and which serves for receiving a stopper element 22, an inserter element 23 and an anchor, e.g. the anchor 1, 10 of FIG. 8. The distal end of the cannula 21 may have a tapered or straight form. The elements 22 and 23 are arranged such in the cannula 21 that they are movable relative to each other. The stopper element 22 has at its distal end a stopper face 22a and includes a boring 22b through which the inserter element 23 and the ends 10a, 10b of the filament 10 extend. The inserter element 23, which has here the form of a rod, comprises an end 23a to act on the anchor 1, 10. The member 1 is arranged in a U-shaped form along the end 23a of the inserter element 23

In use, the elements 22, 23 together with the anchor 1, 10 are moved forward, such that the member 1 and the end 23a emerge out of the cannula 21 and into the cavity, where the anchor 1 is to be applied. Subsequently, the inserter element 23 is retracted, whereas the stopper element 22 remains at the same position, which is on the cortex, in case the cavity is a hole in bone. Thereby, the anchor 1, 10 abuts the stopper face 22a to ensure that it remains in the cavity. After first pulling the ends 10a, 10b to collapse the member 1, the whole instrument 20 is finally removed.

Figure 13:
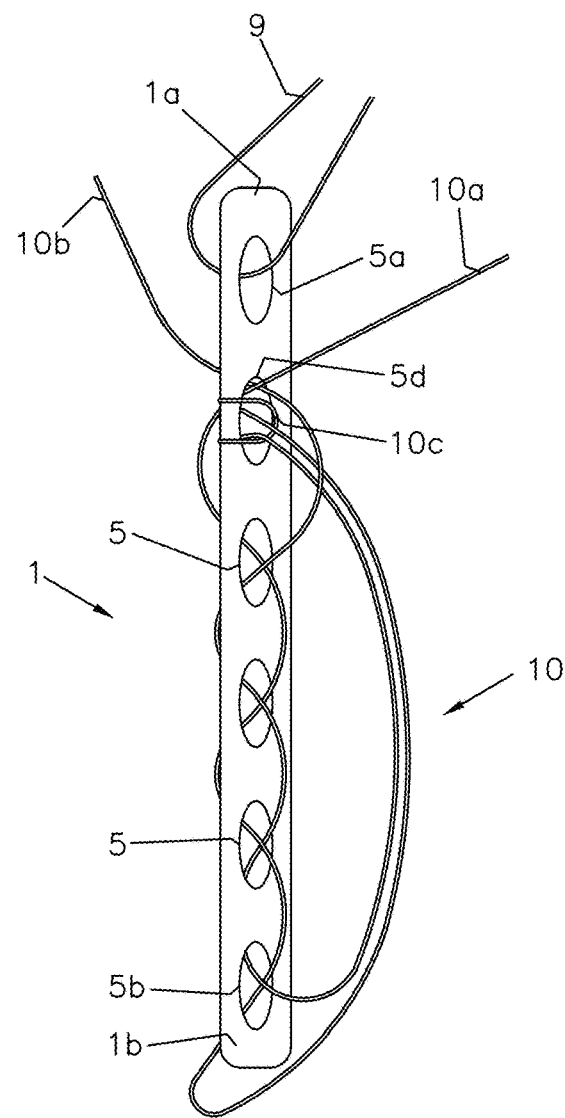
FIG. 13 shows a further embodiment of an anchor of a first kind.

FIG. 13 shows another variant of the anchor. The filament 10 is folded in the middle to form a loop portion 10c arranged at the front side of the member 1. Both ends 10a and 10b of the filament 10 are passed from the rear side of the member 1 through the second eyelet 5d arranged at the end 1a and through the loop portion 10c and are directed through the last eyelet 5b arranged at the end 1b, so that the ends 10a, 10b pass therethrough from opposite sides of the member 1. Subsequently, the two ends 10a, 10b are guided alternatingly through the eyelets 5 from one side of the member 1 to the other side, such that in each case the ends 10a, 10b pass therethrough from opposite sides of the member 1. Finally, the ends 10a, 10b are led through the second eyelet 5d at the end 1a. The anchor comprises a second filament 9, which is guided through the first eyelet 5a at the end 1a, so that it can be shifted as a whole relative to the member 1. In order to facilitate the usage of the anchor, the two filaments 9 and 10 may have for instance different colors.

Figure 15:
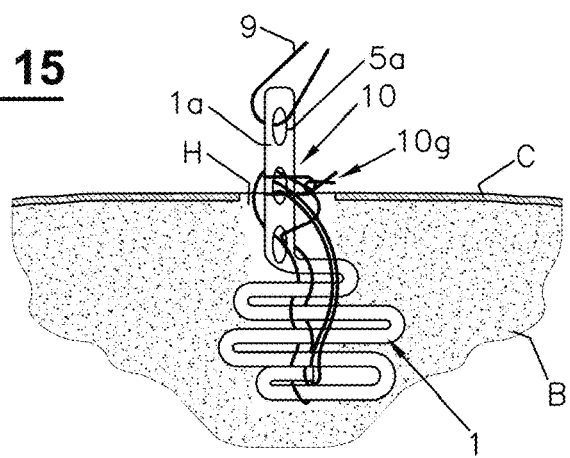
FIG. 15 shows the anchor of FIG. 13 applied in a bone.

In use, the surgeon pushes the member 1 by means of a suitable instrument into a hole H, which is drilled e.g. in the bone of a patient, and pulls on the ends 10a, 10b of the filament 10, so that the member 1 adopts a collapsed structure, see FIG. 15. To firmly seat the anchor in the bone B, the ends 10a, 10b are knotted together alone or by fixing another part forming a knot 10g. The second filament 9, whose ends are arranged outside of the hole H and which is shiftable relative to the member 1, can be used for fixation of another part, such as a ligament, tendon or bone.

Figure 14:
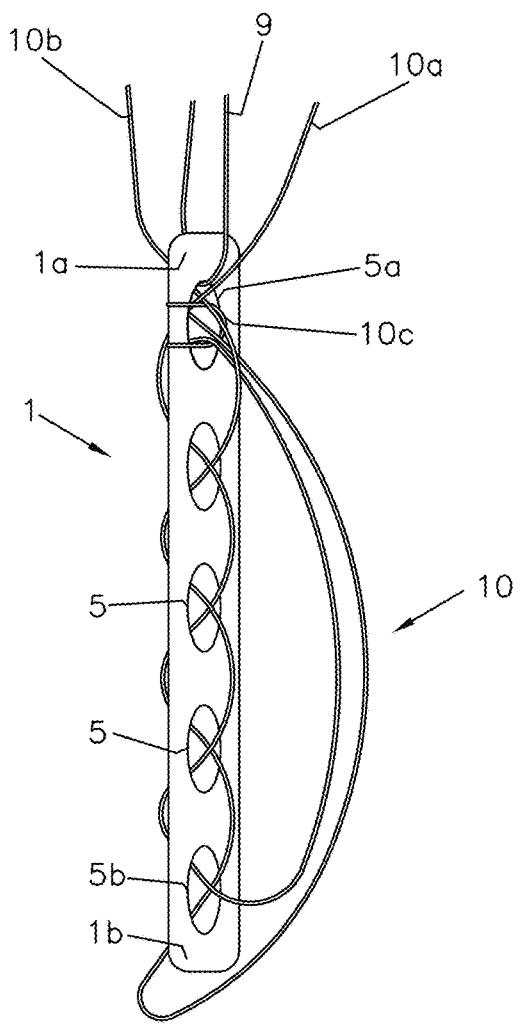
FIG. 14 shows a further embodiment of an anchor of a first kind.

The location, where the second filament 9 is guided through an eyelet, the location with the loop portion 10c and the location, where the free ends 10a, 10b crosses the last time in an eyelet, are in the anchor of FIG. 13 at the first eyelet 5a and the second eyelet 5b, respectively. These locations may be chosen at other eyelets. FIG. 14 shows an example, where said three locations are arranged at the first eyelet 5a.

Figure 16:
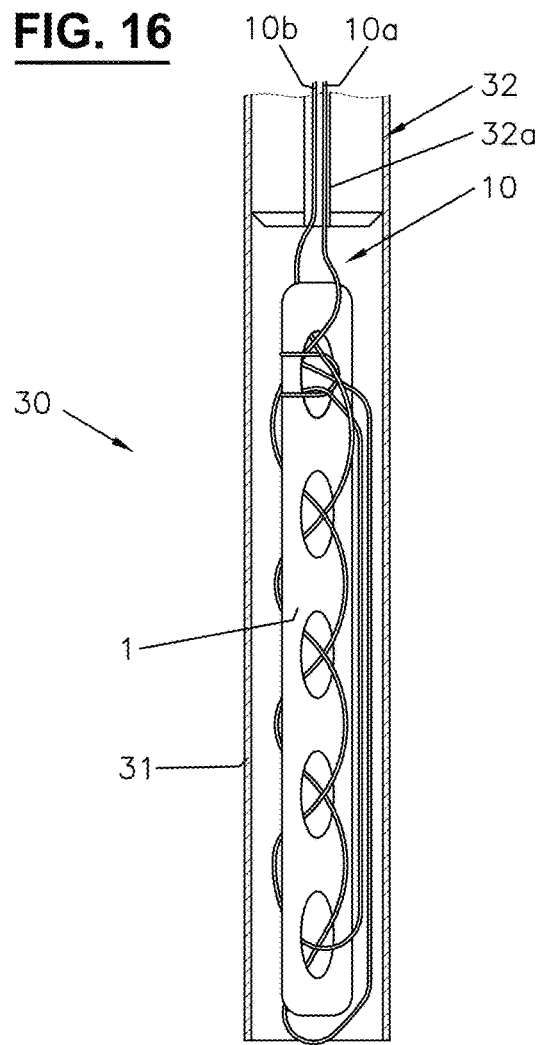
FIG. 16 shows a set with an instrument and an anchor of a first kind in a partly sectioned front view, wherein the instrument and the anchor are shown only in part.

FIG. 16 shows part of an instrument 30 suitable to introduce an anchor in particular in soft tissue of a patient. The instrument 30 may also be used to apply an anchor to hard tissue. It comprises a cannula 31 defining a tube which is open at the distal end and which serves for receiving a pusher element 32 and an anchor, e.g. the anchor 1, 10 of FIG. 14 with or without the second filament 9. The pusher element 32 includes a groove 32a, which extends along its longitudinal axis and in which the ends 10a, 10b of the filament 10 are received. In case, the anchor includes a second filament, e.g. filament 9 in FIG. 14, the groove 32a is configured such that the ends of both filaments 9 and 10 can be accommodated therein.

It is conceivable to provide for more than one groove extending along the axis of the pushing element 32 for receiving the ends of the filament 10 (and of the filament 9 if present). For instance two grooves may be provided, which may be arranged at opposed sides of the pusher element 32, wherein the first end 10a of the filament 10 is received in the first groove and the second end 10a of the filament 10 10 is received in the second groove. If a filament 9 is present, one of its ends may be received in the first groove and its other end in the second groove.

Furthermore, other types of recesses are conceivable for receiving the ends of a filament, e.g. the pusher element 32 may have a bore extending along its longitudinal axis.

In use, the end of the instrument 30 is introduced into the hole, which is formed e.g. in soft tissue, the pusher element 32 is moved forward, so that the anchor is freed out of the interior of the cannula 31. After removing the instrument 30, pulling on the ends 10a, 10b causes the member 1 to collapse.

Embodiments of an Anchor of a Second Kind

Figure 17:
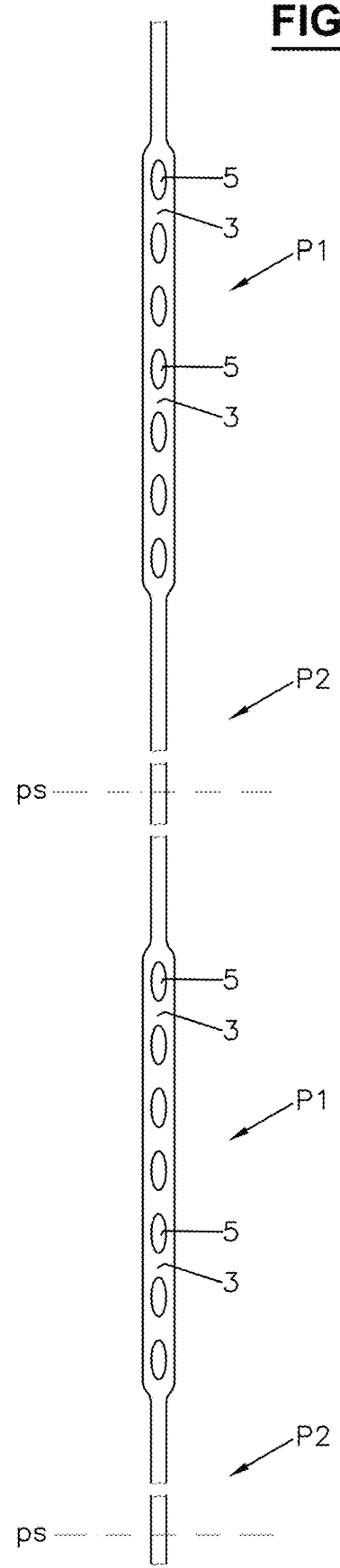
FIG. 17 shows a braided structure for producing an anchor of a second kind.

FIG. 17 shows another example of a flexible slender structure which can be used to form an anchor of a second kind. The structure comprises first parts P1 and second parts P2, which are arranged in an alternating manner along the structure. Each first part P1 comprises a plurality of eyelets 5 passing through the structure, whereas each second part P2 is free of eyelets 5. The second part P2 is similar to a central portion 3 of the first part P1, however with a longer length and, typically, with a smaller width. The number of strands for braiding the second parts P2 may be the same or smaller than the number of strands for braiding the first parts P1. The number of eyelets 5 and their dimension may be chosen with regard to the specific needs of the anchor. The length of a part P2 is greater than that of a part P1, so that it can be passed through eyelets 5 of the part P1 as described further below.

The structure with the parts P1, P2 is braided such that its strands bifurcate and converge to form the parts P2 and the parts P1 with the eyelets 5 and the central portions 3. Similar as in the example of FIG. 2, the parts P1 and P2 have tubular braids with or without a core.

The structure of FIG. 17 may be cut in each case in the middle of each second part P2 (see location ps in FIG. 17) resulting in anchors with a symmetrical form (see FIG. 18).

The anchor shown in FIG. 18 comprises a collapsible member 1 formed by a first part P1 of the structure of FIG. 17 and two filaments 12 and 13 formed by second parts P2 adjacent to the first part P1. As the anchor is braided as a whole, the filaments 12 and 13 are made integral with the member 1. The member 1 has an eyelet 5c in the middle between both ends 1a and 1b, which is left free and which may be used to cooperate with the end 43a of an inserter element 43 (see FIG. 19). The end 12b of the filament 12 is guided through an eyelet 5d adjacent to the eyelet 5c in the middle and then through the following eyelet(s) 5 from one side to the other side of the member 1 up to the eyelet 5a at the end 1a of the member 1. The second filament 13 is arranged in a symmetrical way to the first filament 12 by guiding its end 13b through an eyelet 5e adjacent to the eyelet 5c in the middle and then through the following eyelet(s) 5 from one side to the other side of the member 1 up to the eyelet 5b at the end 1b of the member 1.

In use, pulling on the ends 12b and 13b of the filaments 12 and 13 causes the member 1 to collapse.

FIG. 19 shows part of an instrument 40 suitable to introduce an anchor in particular in hard tissue, such as bone. The instrument 40 may also be used to apply an anchor to soft tissue. It comprises a cannula 41 defining a tube which is open at the distal end and which serves for receiving a stopper element 42, an inserter element 43 and an anchor, e.g. the anchor 1, 12, 13 of FIG. 18. The elements 42 and 43 are arranged such in the cannula 41 that they are movable relative to each other. The stopper element 42 has at its distal end a stopper face 42a and includes a boring 42b through which the inserter element 43 and the ends 12b, 13b of the filaments 12, 13 extend. The inserter element 43, which has here the form of a rod, comprises an end 43a. The anchor 1, 12, 13 is arranged in a U-shaped form within the cannula 41, so that the end 43a of the inserter element 43 can pass through the eyelet 5c in the middle of the member 1.

In use, the surgeon drills with a suitable drill 48 a hole H e.g. into the bone B of a patient as shown in FIG. 20. The cannula 41 of the instrument 40 may be used as a guide for the drill 48 so that the latter moves into the bone B in a defined direction. After removal of the drill 48, the anchor 1, 12, 13 together with the elements 42 and 43 are introduced in the cannula 41 and moved forward until the stopper face 42a of the stopper element 42 abuts on the cortex C. Thereby, the anchor 1, 12, 13 together with the end 43a of the inserter element 43 enters into the hole H, see FIG. 21. Subsequently, the inserter element 43 is retracted, whereby the stopper face 42a ensures that the anchor 1, 12, 13 remains in the hole H. After first pulling the ends 12a, 12b to collapse the member 1, the whole instrument 40 is removed.

Embodiments of an Anchor of a Third Kind

Figure 22:
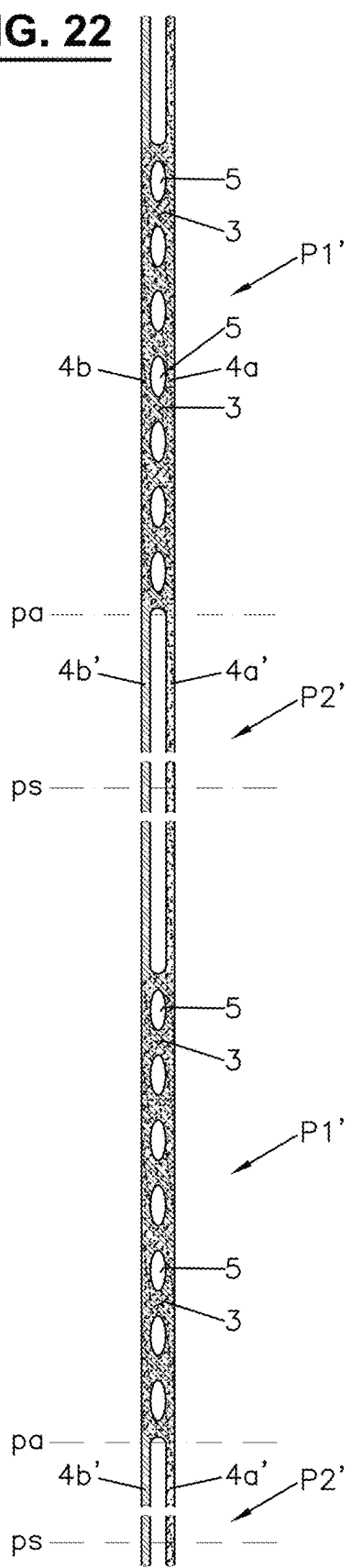
FIG. 22 shows a braided structure for producing an anchor of a third kind.

FIG. 22 shows another example of a flexible slender structure which can be used to form an anchor of a third kind. The structure comprises first parts P1' and second parts P2', which are arranged in an alternating manner along the structure. Each first part P1' comprises a plurality of eyelets 5 passing through the structure, whereas each second part P2' includes two branch portions 4a', 4b'. The second part P2' is similar to the branch portions 4a, 4b of the first part P1', however with a longer length. The length of a part P2' is greater than that of a part P1', so that it can be passed through eyelets 5 of the first part P1' as described further below.

The structure with the parts P1', P2' is braided such that its strands bifurcate and converge to form the parts P2' and the parts P1' with the eyelets 5 and the central portions 3. Similar as in the example of FIG. 2, the parts P1' and P2' have tubular braids with or without a core.

Figure 24:
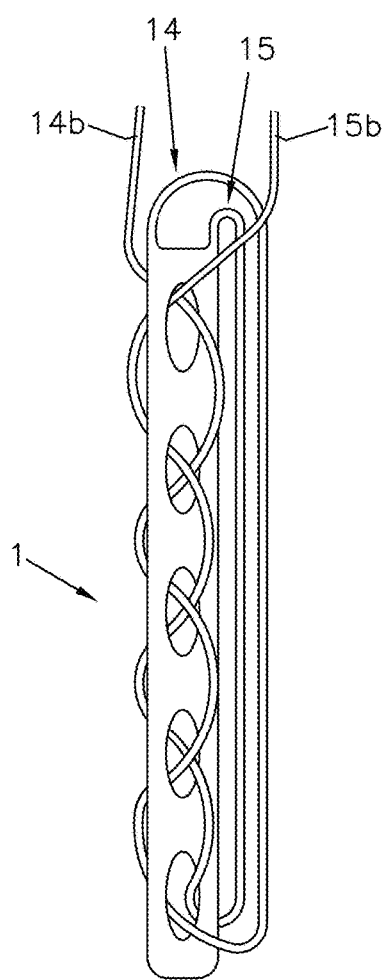
FIG. 24 shows a further embodiment of an anchor of a third kind.
Figure 25:
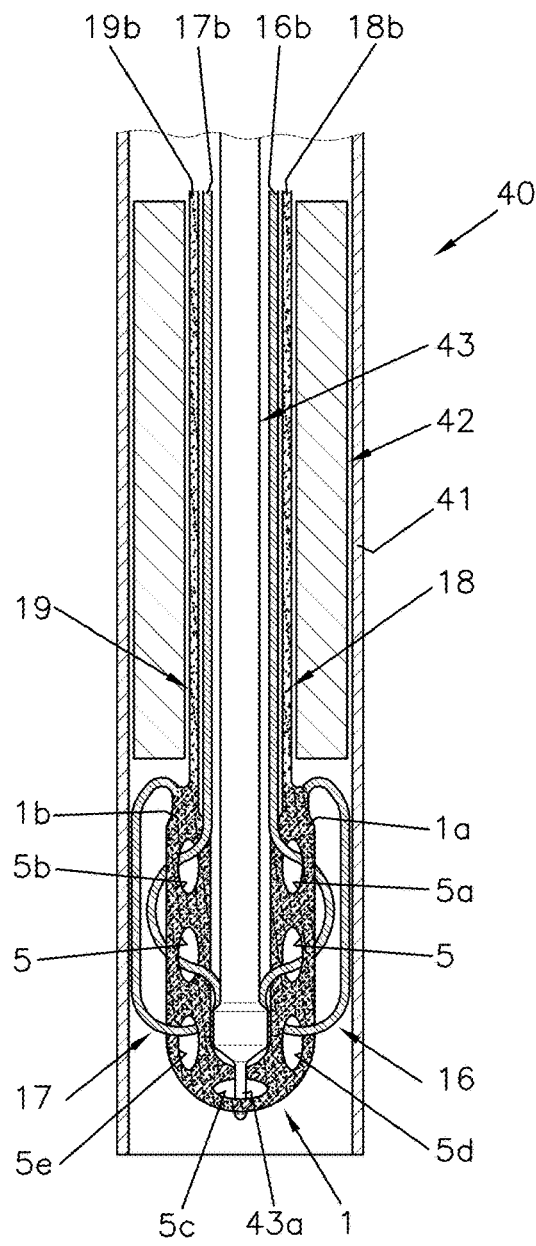
FIG. 25 shows a set with an instrument and an anchor of a third kind in a partly sectioned side view, wherein only part of the instrument and the anchor is shown.

The structure of FIG. 22 may be cut in each case at one end of the first part P1' (see location pa in FIG. 22) resulting in anchors with an asymmetrical form (see FIGS. 23 and 24) or in the middle of each second part P2' (see location ps in FIG. 22) resulting in anchors with a symmetrical form (see FIG. 25). After cutting, the branch portions 4a', 4b' build free ends for handling. If need be, individual branch portions 4a', 4b' may be cut further to adjust the length. In order to facilitate their distinction, it is conceivable to use strands of different colors for braiding the structure, so that a branch portion 4a' is different in color from a branch portion 4b'. This is illustrated in FIG. 22, in which a branch portions 4b' is displayed hatched and a branch portion 4a' is dotted. The first part P1' is hatched and dotted, since it includes strands of either color.

Figure 23:
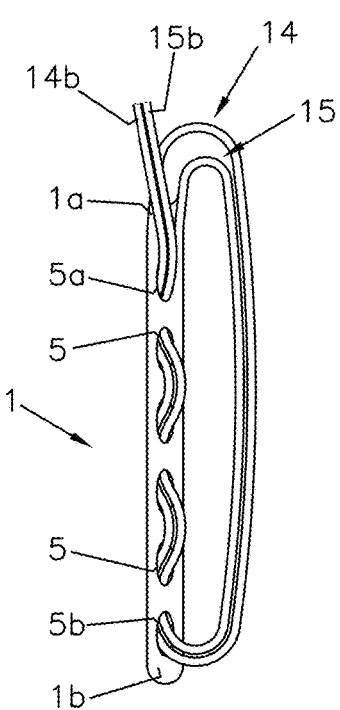
FIG. 23 shows an embodiment of an anchor of a third kind.

The anchor shown in FIG. 23 comprises a collapsible member 1 formed by the first part P1' of the structure of FIG. 22 and two filaments 14 and 15 formed by the branch portions 4a', 4b' of the second part P2. As the anchor is braided as a whole, the filaments 14 and 15 are made integral with the member 1. The filaments 14 and 15 are passed through the last eyelet 5b arranged at the end 1b of the member 1 and then in a parallel manner through the following eyelets 5 from one side to the other side of the member 1 up to the first eyelet 5a at the end 1a of the member 1. In use, pulling on the ends 14b, 15b of the filaments 14, 15 causes the member 1 to collapse.

The filaments 14 and 15 may also be interconnected in another way with the member 1. FIG. 24 shows one example, wherein the filaments 14 and 15 pass not from the same side of the member 1 through an eyelet as in FIG. 23, but from opposite sides.

FIG. 25 shows another example of an anchor received in the instrument 40. The anchor comprises a collapsible member 1 formed by the first part P1' of the structure of FIG. 22 and four filaments 16-19, two per side, formed by second parts P2'. As the anchor is braided as a whole, the filaments 16-19 are made integral with the member 1. The member 1 has an eyelet 5c in the middle between both ends 1a and 1b, which is left free and which may be used to cooperate with the end 43a of the inserter element 43. The end 16b of the filament 16 is guided through an eyelet 5d adjacent to the eyelet 5c in the middle and then through the following eyelet(s) 5 from one side to the other side of the member 1 up to the eyelet 5a at the end 1a of the member 1. The second filament 17 is arranged in a symmetrical way to the first filament 16 by guiding its end 17b through an eyelet 5e adjacent to the eyelet 5c in the middle and then through the following eyelet(s) 5 from one side to the other side of the member 1 up to the eyelet 5b at the end 1b of the member 1. The other two filaments 18 and 19 are not interconnected with the eyelets 5 of the member 1. As indicated in FIG. 25 the color of the filaments 16, 17 is different from the color of the filaments 18, 19. In another embodiment, the filaments 16-19 have the same color.

The anchor 1, 16-19 may be applied in the body of a patient by means of the instrument 40 in an analogous manner as explained above in connection with FIGS. 20 and 21. After first pulling the filaments 16 and 17 to collapse the member 1, the instrument 40 can be removed. The filaments 18 and 19 may be used for a fixation purpose.

Embodiments of an Anchor of a Fourth Kind

Figure 26:
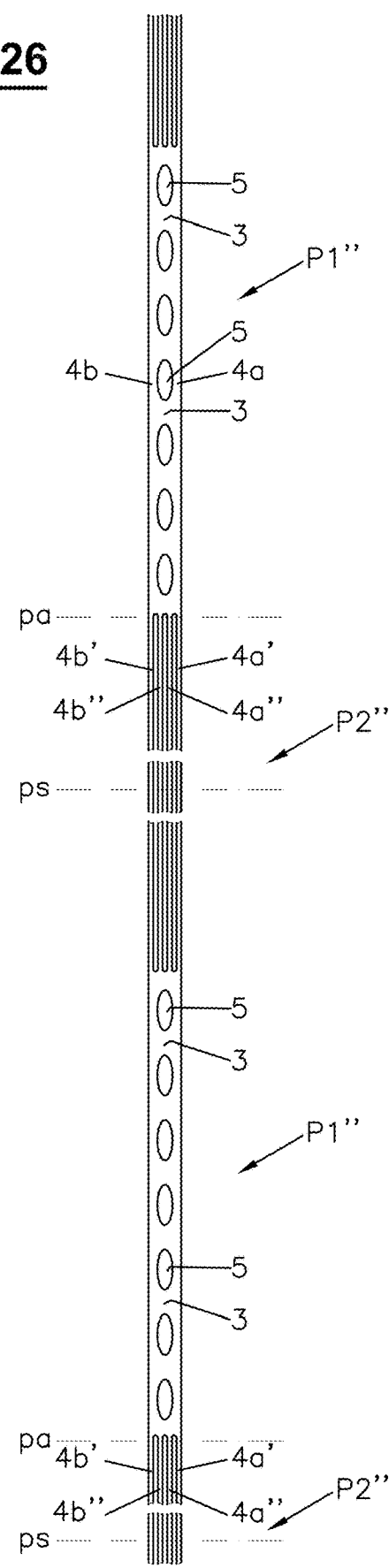
FIG. 26 shows a braided structure for producing an anchor of a fourth kind.

FIG. 26 shows another example of a flexible slender structure which can be used to form an anchor of a fourth kind, which includes a collapsible member with four filaments made integral therewith (instead of two filaments as for anchor of the third kind).

The structure of FIG. 26 comprises first parts P1" and second parts P2", which are arranged in an alternating manner along the structure. Each first part P1" comprises a plurality of eyelets 5 passing through the structure, whereas each second part P2" includes four branch portions 4a', 4a", 4b', 4b". The length of a second part P2" is greater than that of a first part P1", so that it can be passed through eyelets 5 of the first part P1".

The structure with the parts P1", P2" is braided such that its strands bifurcate and converge to form the parts P2" and the parts P1" with the eyelets and the central portions 3. Similar as in the example of FIG. 2, the parts P1" and P2" have tubular braids with or without a core.

The structure of FIG. 26 may be cut in each case at one end of the first part P1" (see location pa in FIG. 26) resulting in anchors with an asymmetrical form or in the middle of each second part P2" (see location ps in FIG. 26) resulting in anchors with a symmetrical form. After cutting, the branch portions 4a', 4a", 4b', 4b" build free ends of filaments. If need be, individual branch portions 4a', 4a", 4b', 4b" may be cut further to adjust the length. Some of the branch portions 4a', 4a", 4b', 4b" may be then guided through eyelets 5 of the first part P1" similar as the filaments 12 to 17 in the anchor of FIGS. 18, 23 to 25 and some of the branch portions 4a', 4a", 4b', 4b" may remain unconnected with the eyelets 5 like the filaments 18 and 19 in the anchor of FIG. 25.

In order to facilitate the distinction of the four filaments of the anchor, it is conceivable to braid the structure such that the color and/or pattern is different for each portion 4a, 4a", 4b', 4b".

As explained above the structures of FIGS. 1, 17, 22 and 26 are made as a fabric in form of a braid. A braid is a structure formed by interlacing strands of flexible material by being placed diagonally to the product axis. Typically, each strand passes alternately over and under each other always in opposite direction. The braid may be two dimensional or three dimensional. In the latter case, a strand runs through the braid in all three directions. All or at least some of the strands of the structures of FIGS. 1, 17, 22 and 26 extend through the whole structure. In order to vary the thickness, some strands may not run through the whole structure of FIGS. 1, 17 and 22, so that the number of strands may be different at different cross-sections of the structure.

Braiding leads to a structure having a high strength. The strands are interlaced such that they do not get separated from each other when for instance a force acts on the location of the bifurcation or convergence of an eyelet 5. The location of bifurcation/convergence can be reinforced e.g. if necessary with an additional thermal in line process after the braiding.

The structures of FIGS. 1, 17, 22 and 26 may be fabricated by means of a braiding machine comprising bobbin carriers which carry the bobbins with the rewound raw material, which forms the strands, as called here. In the braiding operation, the bobbins are advanced along specific tracks of travel, see e.g. EP 2 492 385 A2.

Generally, braiding leads to a different structure then e.g. weaving, where the strands are interlaced at right angles to form the textile, or knitting, where multiple loops of the strands are created.

In order to be suitable for implanting in the human body, biocompatible material is used for the anchor. A strand to be used for braiding includes a monofilament or a multifilament of the same or different type of materials. Examples of suitable materials are:

chemical fibers, e.g. ultra-high-molecular-weight polyethylene, polyester, polypropylene, polyamide
natural fibers, e.g. silk, flax, hemp
metallic fibers, e.g. nickel titanium (Nitinol)
biodegradable fibers, e.g. polylactic acid (PLA), polyglycolic acid (PGA).

It is also possible to combine different types of material to produce the structures of FIGS. 1, 17, 22 and 26, e.g. polyester with polyamide, polyester with hemp, flax with silk, etc.

A fiber may be formed as a single yarn or as multiple yarns, which are twisted together or are combined without twist.

Individual components of the structure of FIGS. 1, 17, 22 and 26, i.e. fiber, yarn, strand, core, etc., or the whole structure may be provided with an additional layer obtained e.g. by impregnating a substance or by plasma deposition.

The anchors described herein have diverse medical applications. They may serve for any type of tissue fastening or securement application, in particular any hard and/or soft tissue-to-tissue securement, tissue-to-device securement, and any other tissue securement application. The anchors may be used to establish a strong point of connection for securing elements relative to a tissue location in a patient or to secure two or more tissue portions together.

In particular, the anchors described herein may be used to fix for instance a tendon to a bone, a ligament to a bone, a bone to a bone, a tendon to a tendon, a tear in a cartilage-like structure, etc. The anchors may be used e.g. in the shoulder, in particular for restoration of the rotator cuff, for example when reattaching soft tissue to bone. Other areas of application are in the knee, in particular for meniscal repair, in the hip, in particular for acetabular labral repair, in the treatment of syndesmosis injuries and in osteosynthesis, in particular for fixation of plates, or of a bone with another bone. In case of poor bone quality, a screw drilled therein may not hold anymore, whereas an anchor described herein may ensure still a reliable fixation.

From the preceding description, many modifications are available to the skilled person without departing from the scope of the invention, which is defined in the claims.

For instance it is conceivable to braid a collapsible member together with any filament attached thereon in an individual manner, instead of producing an endless structure as shown in FIG. 1, 17, 22, 26 which are cut apart.

The invention claimed is:

1. An implantable textile anchor, comprising:
   a collapsible member including a first end, a second end, and a plurality of eyelets arranged between the first end and the second end, the collapsible member being a braided structure between the first end and the second end, the braided structure forming alternatingly tubular central portions and bifurcating and converging tubular branch portions, which define the eyelets, wherein each of the bifurcating and converging tubular branch portions are an individual braided tubular structure, and
   at least one filament, which is guided through eyelets of the collapsible member so that by pulling on the at least one filament the collapsible member collapses to a form with an increased lateral extension.

2. The implantable textile anchor according to claim 1, wherein the at least one filament is knotted to a first eyelet arranged at the first end of the collapsible member, guided through a second eyelet arranged at the second end of the collapsible member and through eyelets arranged between the first and second eyelets.

3. The implantable textile anchor according to claim 2, wherein the at least one filament is separate from the collapsible member and guided through eyelets such that both ends of the filament are accessible for pulling thereon.

4. The implantable textile anchor according to claim 2, comprising another filament, which is separate from the collapsible member and interconnected therewith such that the another filament is shiftable as a whole relative to the collapsible member.

5. The implantable textile anchor according to claim 1, wherein the at least one filament is separate from the collapsible member and guided through eyelets such that both ends of the filament are accessible for pulling thereon.

6. The implantable textile anchor according to claim 5, comprising another filament, which is separate from the collapsible member and interconnected therewith such that the another filament is shiftable as a whole relative to the collapsible member.

7. The implantable textile anchor according to claim 1, comprising another filament, which is separate from the collapsible member and interconnected therewith such that the another filament is shiftable as a whole relative to the collapsible member.

8. The implantable textile anchor according to claim 1,
   wherein the at least one filament comprises first and second filaments,
   wherein the first and second filaments are braided filaments, and
   wherein, for cooperating with an end of an inserter element, an eyelet arranged between the first end and the second end of the collapsible member is left free from guiding the first and second filaments therethrough.

9. The implantable textile anchor according to claim 1, comprising at least four filaments made integral with the collapsible member by braiding the collapsible member and the filaments together.

10. The implantable textile anchor according to claim 1, wherein an interior of the tubular central portions and tubular branch portions include a core.

11. A set comprising at least one implantable textile anchor according to claim 1 and an instrument for implanting the anchor, the instrument comprising a cannula for receiving the anchor as well as at least one element, which is movable relative to the cannula for acting on the anchor.

12. The set according to claim 11, wherein the element comprises at least one recess extending along the element for receiving part of the at least one filament.

13. The set according to claim 11, wherein the element is an inserter element, whose end cooperates with the anchor and which extends through a boring in a stopper element, the inserter element and the stopper element being arranged movably relative to each other.

14. A method for producing an implantable textile anchor according to claim 1, in which a continuous structure comprising eyelets is braided and pieces are cut off providing a collapsible member.

15. The method of claim 14, wherein the continuous structure has alternatingly a first portion, which comprises eyelets and which defines a collapsible member, and a second portion, which is free of eyelets and which define one or more filaments made integral with the collapsible member.

16. The method of claim 15, wherein pieces including first and second portions are cut off from the continuous structure in a symmetrical way such that a second portion is arranged at each end of the first portion of a piece or in an asymmetrical way such a second portion is arranged only at one end of the first portion of a piece.

17. The implantable textile anchor according to claim 1, wherein the at least one filament is knotted to an eyelet.

18. The implantable textile anchor according to claim 1, wherein the at least one filament and at least a second filament are made integral with the collapsible member by braiding the collapsible member and the filaments together.

19. The implantable textile anchor according to claim 18, wherein the at least one filament is attached to the first end of the collapsible member and the at least a second filament is attached to the first end or to the second end of the collapsible member.

20. The implantable textile anchor according to claim 18, wherein the at least one filament is guided through eyelets arranged at the first end and the at least a second filament is guided through eyelets arranged at the second end of the collapsible member.

* * * * *